United States Patent [19]

Hoornaert et al.

[11] Patent Number: 5,483,572
[45] Date of Patent: Jan. 9, 1996

[54] X-RAY EXAMINATION APPARATUS

[75] Inventors: Bart P. A. J. Hoornaert; Adrianus C. Van Benthem, both of Eindhoven, Netherlands

[73] Assignee: U.S. Philips Corporation, New York, N.Y.

[21] Appl. No.: 214,388

[22] Filed: Mar. 14, 1994

[30] Foreign Application Priority Data

Mar. 12, 1993 [EP] European Pat. Off. .............. 93200739

[51] Int. Cl.$^6$ .................................................. G21K 3/00
[52] U.S. Cl. ........................................ 378/156; 378/145
[58] Field of Search ...................................... 378/156–159

[56] References Cited

U.S. PATENT DOCUMENTS

| | | | |
|---|---|---|---|
| 3,932,759 | 1/1976 | Brundin | 378/116 |
| 5,107,529 | 4/1992 | Boone | 378/156 |
| 5,185,775 | 2/1993 | Sirvin | 378/156 |
| 5,287,396 | 2/1994 | Stegehuis | 378/98.2 |

FOREIGN PATENT DOCUMENTS

| | | |
|---|---|---|
| 0343600 | 11/1989 | European Pat. Off. . |
| 0496438 | 7/1992 | European Pat. Off. . |

*Primary Examiner*—Craig E. Church
*Attorney, Agent, or Firm*—Jack D. Slobod

[57] ABSTRACT

Absorption filters are positioned in an x-ray examination apparatus according to the invention by adjusting them on the basis of the posture of the carrier supporting the x-ray source and the x-ray detector. To that end adjustment curves relating carder posture to filter adjustment are employed. The posture of the carder determines the orientation of the x-ray beam path. Because there are relatively few anatomical differences among patients to be examined, the adjustment of absorption filters on the basis of the beam orientation is quite adequate. Further improvement is achieved by providing sets of adjustment curves, each set pertaining to a class of patients, such as e.g. corpulent or slender patients, or infants or adults.

9 Claims, 3 Drawing Sheets

X-RAY EXAMINATION APPARATUS

BACKGROUND OF THE INVENTION

1. Field of the Invention

The invention relates to an x-ray apparatus comprising a carrier supporting an x-ray source for producing an x-ray beam, an x-ray detector facing the x-ray source and an adjustable absorption filter which is arranged between the x-ray source and the x-ray detector, the carrier being moveable to direct the x-ray beam path.

2. Description of the Related Art

An x-ray apparatus of said kind is known from the European patent application EP 0 496 438 which corresponds to U.S. Pat. No. 5,287,396.

An x-ray apparatus as described in the cited European patent application is provided with absorption filters having the form of moveable wedge filters. To prevent areas in an x-ray image from being overexposed, wedge filters are positioned so that very low x-ray absorption areas adjacent to strong x-ray absorption areas are blocked out to some extent. Wedge filters are positioned in the known x-ray examination apparatus on the basis of contour recognition during the formation of the x-ray image. Consequently, complicated image processing means are required.

SUMMARY OF THE INVENTION

It is an object of the invention to provide an x-ray examination apparatus for producing an x-ray image in which overexposed areas are reduced. It is also an object of the invention to reduce a dose of x-radiation required for producing the x-ray image.

To achieve this, an x-ray examination apparatus according to the invention is characterized in that the x-ray examination apparatus is provided with filter-control means for accepting a posture of the carrier and furnishing a position of the absorption filter so as to control the adjustment of the absorption filter.

When a shadow-image is made of a part of a patient's body to be examined by means of x-irradiation, there are areas of the x-ray image in which overexposure is to be avoided in that these areas are blocked out by means of an absorption filter. The location of such areas with respect to a region of interest in the x-ray image is determined by the orientation of the x-ray beam path with respect to the patient. Since anatomical structures show a comparatively limited variation among various patients, the location of areas subjected to risk of overexposure is predominantly determined from the position of the carrier on which the x-ray source and the x-ray detector are mounted. Thus, absorption filters are adequately positioned by providing filter-control means that control the positioning of the moveable absorption filter on the basis of the posture of the carrier. In this manner, with respect to the patient and with respect to a patient support table, protracted irradiation of the patient is avoided when a person operating the x-ray examination apparatus adjusts the absorption filter. Thus, subjection of both patient on operating personnel to harmful x-radiation is reduced.

A preferred embodiment of an x-ray examination apparatus in according to the invention is characterized in that the filter-control means comprises a memory device for storing pairs of position data, a pair consisting of a position data of the absorption filter and a posture of the carrier.

The filter-control means is further adequately operated by providing a memory device in which positions of the carrier and corresponding position adjustment data of the absorption filter are stored. These data constitute one or several adjustment curves which represent the positioning of the absorption filter on the basis of the posture of the carrier.

A further preferred embodiment of an x-ray examination apparatus according to the invention is characterized in that the filter-control means is arranged to furnish a translation of the absorption filter with respect to the x-ray beam path from said posture of the carrier.

In particular, overexposure is avoided in an area in the x-ray image in that the absorption filter is moved into the x-ray beam to some extent by translating the absorption filter with respect to the x-ray beam path. In this manner part of the x-my beam is attenuated to some extent.

When the filter-control means is provided with a memory device, then the memory device will preferably contain an adjustment curve representing translation distances of the absorption filter corresponding to postures of the carrier.

A further preferred embodiment of an x-ray examination apparatus according to the invention is characterized in that the absorption filter is rotatable and comprises an x-ray absorbing part and an x-ray transmitting part and that the filter-control means is arranged to furnish an orientation of the absorption filter with respect to an axis of rotation of the absorption filter.

A sophisticated absorption filter comprises an x-ray absorbing part and an x-ray transmitting part which has the shape of a section of a substantially circular disk and such an absorption filter is slidable into or out of the x-ray beam path and is in addition rotatable about an axis of rotation making right angles to the plane of the disk section. By rotating of the absorption filter being within in or close to the x-ray beam path, portions of the x-ray beam having a comparatively more complicated form can be blocked out. In an x-ray examination apparatus in according to the invention, the absorption filter is controlled by the filter control means so as to adequately position the absorption filter and block out a relevant portion of the x-ray beam. When the filter-control means is provided with a memory device, this memory device will preferably contain an adjustment curve representing orientation angles of the absorption filter corresponding to postures of the carrier.

A further preferred embodiment of an x-ray examination apparatus according to the invention is characterized in that the memory device is arranged to store a plurality of sets of said pairs of position data, each set corresponding to a class of objects to be examined.

Although the anatomical structure of various patients may be comparatively similar, there is some variation between various groups of patients, such as e.g. corpulent or slender patients or adults or infants. When patients from either group are examined, an even more adequate adjustment of the absorption filter is achieved when various adjustment curves are provided in said memory device, each adjustment curve pertaining to one of said groups of patients.

These and other aspects of the invention will become apparent from and will be elucidated with reference to the embodiments described hereinafter and with reference to the accompanying drawings.

DETAILED DESCRIPTION OF THE PREFERRED EMBODIMENTS

Figure 1:
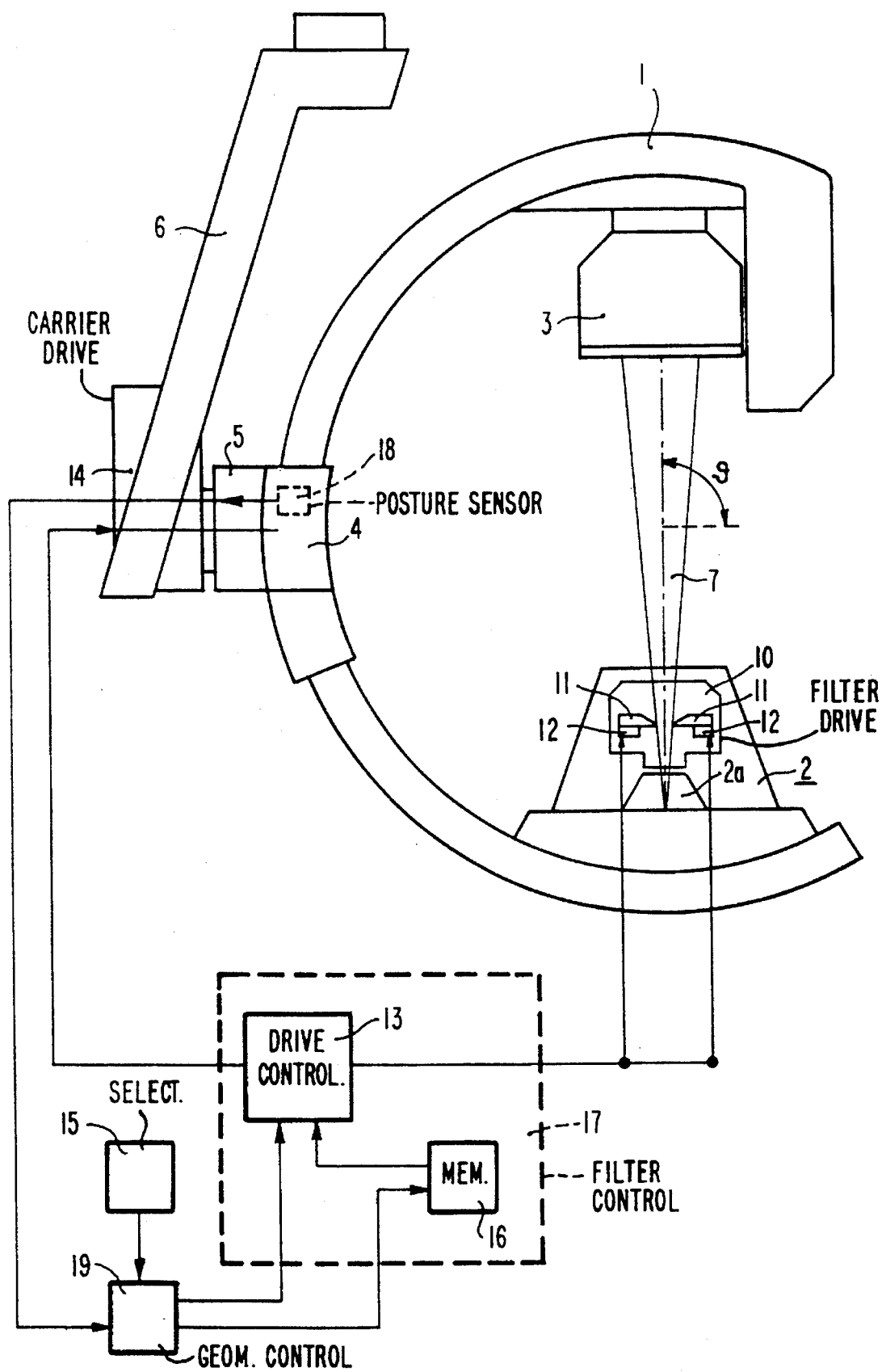
FIG. 1 shows a schematic diagram of an x-ray apparatus according to the invention.

FIG. 1 shows a schematic diagram of an x-ray apparatus according to the invention. A carrier 1 in the form of a C-shaped arm carrier supports an x-ray source unit 2 and an x-ray detector 3 in the form of an x-ray image intensifier facing the x-ray source unit. The carrier is moveable through a sleeve 4 and by means of a bearing 5. The carrier is attached by way of the bearing 5 to a predominantly vertical stand 6 which is rotatably mounted to a ceiling of a room in which the x-ray apparatus is set up. Thus, the x-ray source unit and the x-ray detector are moveable so as to orient a beam-path 7 of x-radiation emitted by the x-ray source unit so that various projections can be applied for making an x-ray image. A falter-arrangement 10 comprising absorption filters 11 and filter-drive-means 12 is incorporated in the x-ray source unit 2, the filter-arrangement 10 being positioned between the x-ray source 2a and the x-ray detector 3. When an x-ray image is being made, overexposure in certain areas of the x-ray image is to be avoided. Overexposure is liable to occur when regions of very low x-ray absorption and adjacent regions of high x-ray absorption are imaged in the same x-ray image. For instance, when imaging a patient's heart having a high x-radiation absorption, the surrounding lung-tissue having a low x-ray absorption will be overexposed. By covering regions of high x-ray transmittance by positioning absorption filters 11 in the x-ray beam path 7 overexposure by regions of high transmittance are avoided.

Correct positioning of the absorption filters depends on the orientation of the x-ray beam-path with respect to an object that is being examined, because the object is imaged according to a projection corresponding to the orientation of the beam-path. Filter-drive-means 12 are provided for positioning the absorption filters 11. The filter-drive-means are connected to drive-control-means 13 to which also carrier-drive-means 14 are coupled. For orientating the beam-path 7 and adjusting the absorption filters accordingly, a selection-means 15 is provided for supplying a positioning signal to a geometry controller 19. Furthermore, a posture sensor 18 is further provided to produce a posture signal pertaining to the position of the carrier. The posture signal is supplied to the geometry-controller. The geometry-controller 19 supplies a positioning signal to the drive-control-means 13, for positioning the carrier 1 in correspondence with a required beam-path orientation. The carrier-drive means 14 is controlled by the drive-control-means 13 for displacing the carrier 1. The geometry-controller 19 also applies said positioning signal to a memory-device 16 for selecting a filter-position. To this end, one or a plurality of filter-position curves is stored in the memory-device 16; each of the filter-position curves represents filter-adjustments as a function of the position of the carrier 1. When a positioning signal is supplied to the memory-device 16, a filter-adjustment signal is supplied by the memory-means to the drive-control-means 13. In this manner, filter-control-means 17 is constituted by the drive-control-means in combination with the memory device 16. Subsequently, the drive-control-means controls the filter-drive-means 12 so as to adequately position the absorption filters 11.

Figure 2:
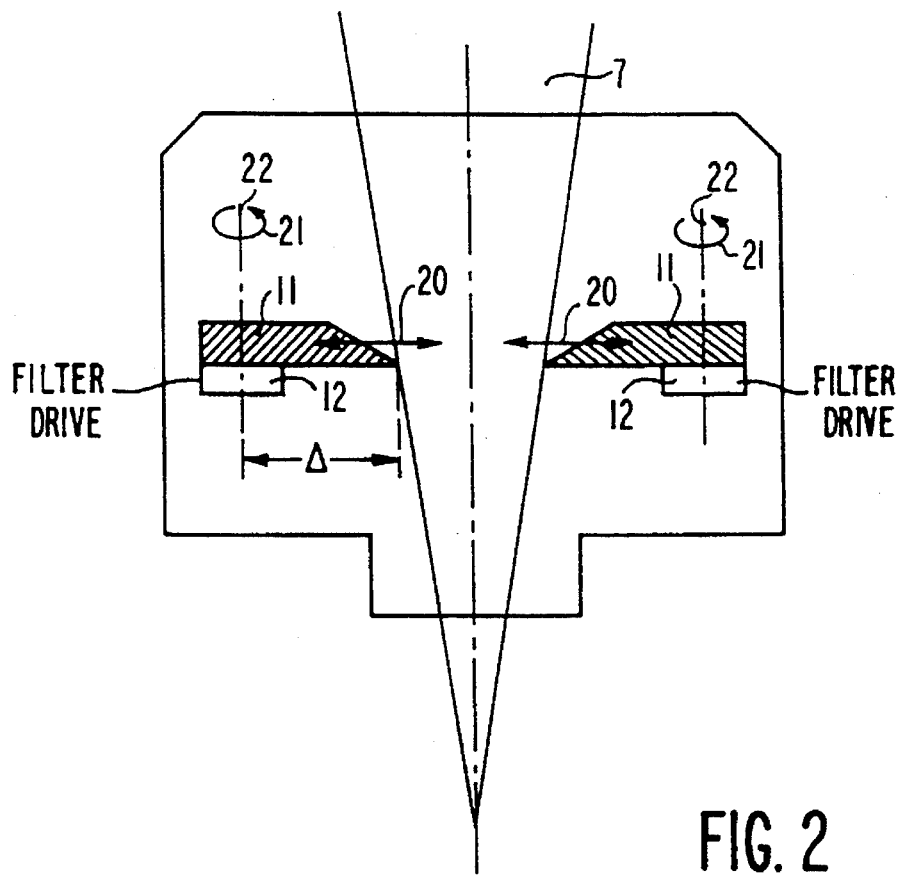
FIG. 2 shows a side elevation of a filter-arrangement for use in an x-ray apparatus according to the invention.

The positioning of the absorption filters will be described in more detail with reference to FIGS. 2 and 3. FIG. 2 shows a side elevation of a filter-arrangement for use in an x-ray apparatus according to the invention. The absorption filters have a wedge-shaped extremity so that a gradual transition between a covered region and an uncovered region is obtained and consequently steep gradients in the x-ray image are avoided. The absorption filters are mounted to filter-drive-means 12 in such a way that the filters are moveable into and out of the x-ray beam path 7 as indicated by arrows 20. Furthermore the absorption filters are rotatable about axes 22 as indicated by arrows 21.

Figure 3:
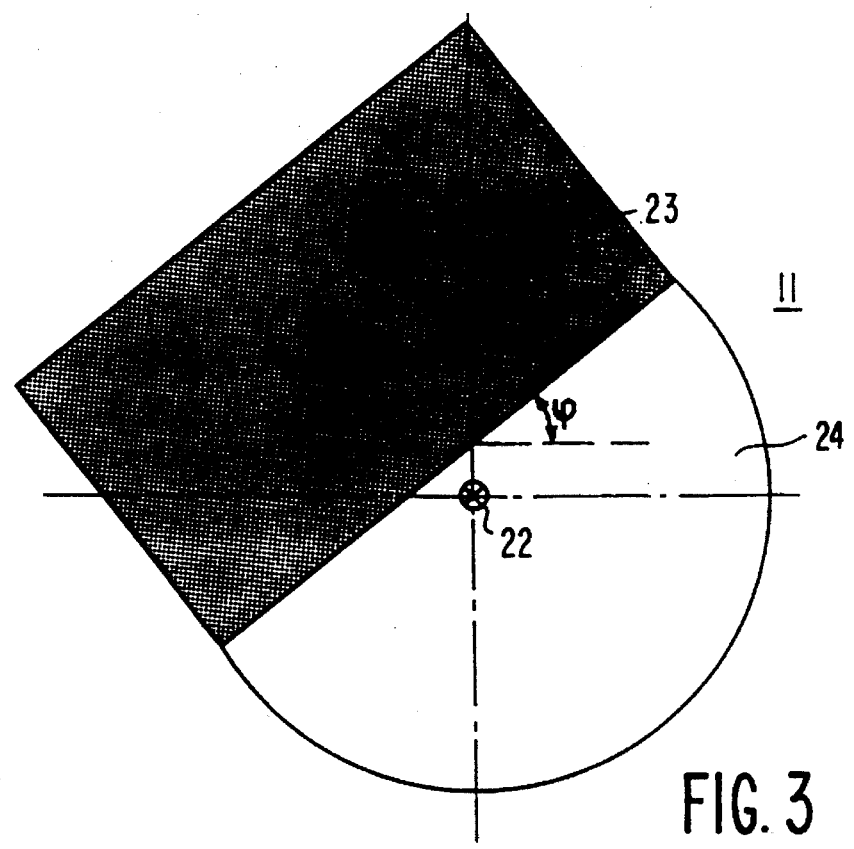
FIG. 3 shows a top view of an absorption filter incorporated in a filter-arrangement shown in FIG. 2.

FIG. 3 shows a top view of an absorption filter incorporated in a filter-arrangement shown in FIG. 2. The absorption filter has an x-ray absorbing part 23, e.g. containing lead, and an x-ray transmitting part 24 which has the shape of a section of a substantially circular disk. Thus, when rotating either one of the absorption filters 11 about its axis 22 the part of the x-ray beam that impinges on the absorption filter is varied and consequently, the part of the x-ray image being covered by the absorption filter is varied.

Figure 4A:
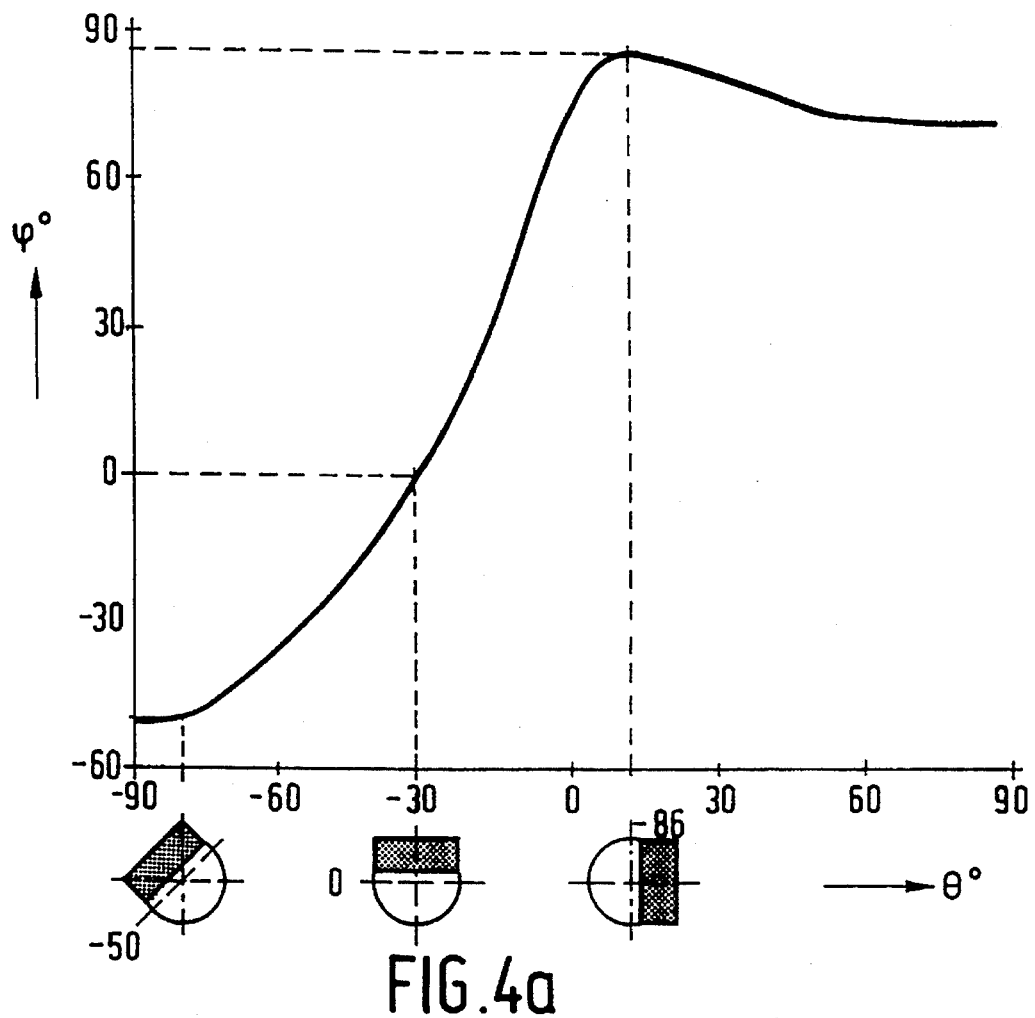
FIG. 4a shows a graph of a first adjustment curve, representing a rotation angle of the absorption filter as a function of beam-path orientation.

FIG. 4a shows a graph of a first adjustment curve, representing a rotation angle of the absorption filter as a function of the beam-path orientation. The rotation angle $\phi$ according to which the absorption filter is positioned is given as a function of the angle $\theta$, which determines the orientation of the beam path with respect to a patient to be examined. For further illustration, a few particular orientations of the absorption filter have been presented as small diagrams, along the abscissa. When the carrier is positioned in accordance with $\theta=-80°$, then the absorption filter is placed in an orientation of $\phi=-50°$. When the carrier is moved so as to change the beam-path orientation to $\theta=10°$, is increased to $\phi=86°$. Finally, when the beam-path orientation angle is increased further, the angle of orientation of the absorption filter is slightly decreased.

Figure 4B:
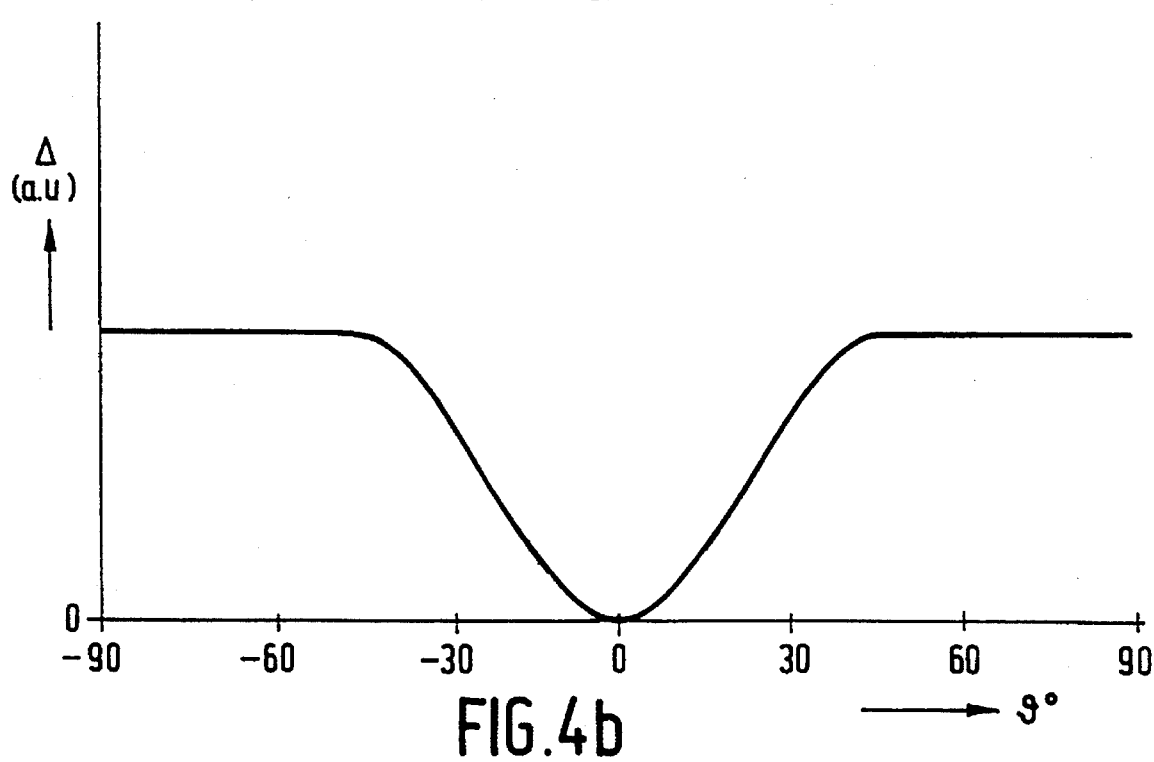
FIG. 4b shows a graph of a second adjustment curve, presenting translation of the absorption filter with respect to the beam-path as a function of beam-path orientation.

FIG. 4b shows a graph of a second adjustment curve, representing translation of the absorption filter with respect to the beam-path as a function of beam-path orientation. As the curve shows, the absorption filter is moved further into the beam-path as the beam path is inclined from perpendicular incidence, viz. $\Delta$ has a minimum when $\theta=0°$ and $\Delta$ increases as $|\theta|$ increases.

The features of the adjustment curves are determined by anatomical properties, notably the location of a heart of a patient with respect to surrounding lungtissue. In practice, these curves can be determined empirically, viz. by manually positioning absorption filters, for a multitude of carder orientations, so as to obtain optimum image quality. It appears that a single set of adjustment curves is already quite satisfactory for a multitude of patients. Further improvement can, however, be achieved by determining sets of adjustment curves, each set pertaining to a class of patients, such as corpulent or slender patients, adults or infants, etc.

We claim:

1. An x-ray apparatus comprising a carrier supporting an x-ray source for producing an x-ray beam, an x-ray detector facing the x-ray source and an adjustable absorption filter which is arranged between the x-ray source and the x-ray detector, the carrier posture being variable to alter orientation of the x-ray beam path, characterized in that the x-ray examination apparatus is provided with filter-control means for accepting a posture of the carrier and furnishing a position of the absorption filter so as to control adjustment of the absorption filter in dependence upon the posture of the carrier.

2. An x-ray examination apparatus as claimed in claim 1, characterized in that the filter-control means comprises a memory device for storing pairs of position data, a pair consisting of a position data of the absorption filter and a posture of the carrier.

3. An x-ray apparatus as claimed in claim 1, characterized in that the filter-control means is arranged to furnish a translation of the absorption filter with respect to the x-ray beam path from said posture of the carrier.

4. An x-ray apparatus as claimed in claim 1, characterized in that absorption filter is rotatable and comprises an x-ray absorbing part and an x-ray transmitting part and that the filter-control means is arranged to furnish an orientation of the absorption filter with respect to an axis of rotation of the absorption filter.

5. An x-ray examination apparatus as claimed in claim 2, characterized in that the memory device is arranged to store a plurality of sets of said pairs of position data, each set corresponding to a class of objects to be examined.

6. An x-ray apparatus as claimed in claim 2, characterized in that the filter-control means is arranged to furnish a translation of the absorption filter with respect to the x-ray beam path from said posture of the carrier.

7. An x-ray apparatus as claimed in claim 5, characterized in that the filter-control means is arranged to furnish a translation of the absorption filter with respect to the x-ray beam path from said posture of the carrier.

8. An x-ray apparatus as claimed in claim 2, characterized in that absorption filter is rotatable and comprises an x-ray absorbing part and an x-ray transmitting part and that the filter-control means is arranged to furnish an orientation of the absorption filter with respect to an axis of rotation of the absorption filter.

9. An x-ray apparatus as claimed in claim 5, characterized in that absorption filter is rotatable and comprises an x-ray absorbing part and an x-ray transmitting part and that the filter-control means is arranged to furnish an orientation of the absorption filter with respect to an axis of rotation of the absorption filter.

* * * * *